United States Patent
Wang et al.

(10) Patent No.: US 10,145,810 B2
(45) Date of Patent: Dec. 4, 2018

(54) USING NMR RESPONSE DEPENDENCE ON GAS PRESSURE TO EVALUATE SHALE GAS STORAGE

(71) Applicant: Chevron U.S.A. Inc., San Ramon, CA (US)

(72) Inventors: Haijing Wang, Sugar Land, TX (US); Scott Jeffrey Seltzer, Houston, TX (US); Boqin Sun, Houston, TX (US)

(73) Assignee: CHEVRON U.S.A. INC., San Ramon, CA (US)

( * ) Notice: Subject to any disclaimer, the term of this patent is extended or adjusted under 35 U.S.C. 154(b) by 643 days.

(21) Appl. No.: 14/673,043

(22) Filed: Mar. 30, 2015

(65) Prior Publication Data
US 2016/0290942 A1 Oct. 6, 2016

(51) Int. Cl.
G01N 24/08 (2006.01)
G01R 33/44 (2006.01)
G01V 3/32 (2006.01)

(52) U.S. Cl.
CPC ......... *G01N 24/081* (2013.01); *G01N 24/082* (2013.01); *G01R 33/448* (2013.01); *G01V 3/32* (2013.01)

(58) Field of Classification Search
CPC .................................................... G01N 24/08
(Continued)

(56) References Cited

U.S. PATENT DOCUMENTS

| 6,032,101 | A | 2/2000 | Freedman et al. |
| 7,417,426 | B2 * | 8/2008 | Race ....................... G01N 24/08 324/303 |
| 7,684,939 | B2 * | 3/2010 | Allende-Blanco ......................... G06F 17/5018 702/33 |
| 8,738,295 | B2 * | 5/2014 | Baez ....................... E21B 49/00 702/11 |
| 8,857,194 | B1 * | 10/2014 | Sutterlin ................... C09K 5/00 62/4 |

(Continued)

FOREIGN PATENT DOCUMENTS

WO  2011/133859 A1  10/2011
WO  2013/023011 A2  2/2013

(Continued)

OTHER PUBLICATIONS

Bowers, M. C. et al, Journal of petrolium Science and Engineering 1995, 13, 1-14.*

(Continued)

*Primary Examiner* — Arlen Soderquist

(57) ABSTRACT

A disclosed method for characterizing gas adsorption on a rock sample includes: measuring a nuclear magnetic resonance (NMR) response of the rock as a function of surrounding gas pressure along an isotherm; transforming the NMR response to obtain a Langmuir pressure distribution of gas adsorption on the rock sample; and displaying the Langmuir pressure distribution. The Langmuir pressure distribution may be shown in one dimension (e.g., contribution to signal response versus Langmuir pressure), or may be combined with additional pressure-dependencies such as spin-lattice relaxation time ($T_1$), spin-spin relaxation time ($T_2$), and chemical shift ($\delta$) to form a multi-dimensional distribution. The method can further include: identifying peaks in the Langmuir pressure distribution; and associating a gas storage mechanism and capacity with each peak. It may still further include: exposing the rock sample to a treatment fluid to obtain an altered sample; repeating said measuring and transforming operations with the altered sample; and comparing the Langmuir pressure distributions to determine effects of the treatment.

27 Claims, 15 Drawing Sheets

(58) Field of Classification Search
USPC .................................................. 436/25, 31
See application file for complete search history.

(56) References Cited

U.S. PATENT DOCUMENTS

| | | | | |
|---|---|---|---|---|
| 9,599,581 | B2* | 3/2017 | Kwak | ............... G01N 11/00 |
| 2004/0189296 | A1 | 9/2004 | Sun et al. | |
| 2007/0210798 | A1* | 9/2007 | Race | ............... G01N 24/08 324/321 |
| 2011/0282062 | A1* | 11/2011 | Hattori | ............... C07F 9/65583 546/23 |
| 2011/0282584 | A1* | 11/2011 | Baez | ............... E21B 49/00 702/13 |
| 2012/0192640 | A1 | 8/2012 | Minh et al. | |
| 2012/0318533 | A1* | 12/2012 | Keller | ............... E21B 41/0064 166/402 |
| 2014/0088878 | A1 | 3/2014 | Chen et al. | |
| 2014/0229112 | A1 | 8/2014 | Datey et al. | |
| 2014/0232391 | A1 | 8/2014 | Kadayam Viswanathan et al. | |
| 2014/0320126 | A1 | 10/2014 | Heaton et al. | |
| 2016/0313267 | A1* | 10/2016 | Kwak | ............... G01N 11/00 |

FOREIGN PATENT DOCUMENTS

| | | |
|---|---|---|
| WO | 2013/148516 A1 | 10/2013 |
| WO | 2013/184404 A1 | 12/2013 |

OTHER PUBLICATIONS

Leisen, J. et al, Solid State Nuclear Magnetic Resonance 2002, 22, 409-422.*
Sigal, R. F. et al, Petrophysics 2011, 52, 32-49.*
Gasparik, M. et al, Energy & Fuels 2012, 26, 4995-5004.*
Horch, C. et al, Journal of Magnetic Resonance 2014, 240, 24-33.*
Rexer, T. F. et al, Energy & Fuels 2014, 28, 2886-2901.*
Misra, D. N., Surface Science 1969, 18, 367-372.*
Rudzinski, W. et al, Surface Science 1974, 42, 552-564.*
Pape, H. et al, Pure and Applied Geophysics 2009, 166, 1125-1163.*
Zhao, Y.-L. et al, Journal of Petroleum Science and Engineering 2013, 110, 253-262.*
Anderson, Robert J., et al.; "NMR Methods of Characterizing the Pore Structures and Hydrogen Storage Properties of Microporous Carbons"; J. Am. Chem. Soc., 2010, vol. 132, pp. 8618-8626.
Kausik, Ravinath, et al.; "Characterization of Gas Dynamics in Kerogen Nanopores by NMR"; Oct.-Nov. 2011, SPE 147198, pp. 1-16.
Mitchell, J., et al.; "Nuclear Magnetic Resonance Cryoporometry"; 2008, Physics Reports, vol. 461, pp. 1-36.
Musharfi, Nedhal, et al.; "Combining Wireline Geochemical, NMR, and Dielectric Data for Formation Evaluation and Characterization of Shale Reservoirs"; SPWLA 53$^{rd}$ Annual Logging Symposium, Jun. 2012, pp. 1-16.
Peterson, Ronald W., et al.; "Self Contained High Pressure Cell, Apparatus and Procedure for the Preparation of Encapsulated Proteins Dissolved in Low Viscosity Fluids for NMR Spectroscopy"; Sep. 2005, Rev. Sci. Instrum., 76(9); pp. 1-7.
Song, Y.-Q., et al.; "$T_1$-$T_2$ Correlation Spectra Obtained Using a Fast Two-Dimensional Laplace Inversion"; 2002, Journal of Magnetic Resonance, vol. 154, pp. 261-268.
Sun, Boqin, et al.; "A Global Inversion Method for Multi-Dimensional NMR Logging"; 2005, Journal of Magnetic Resonance, vol. 172, pp. 152-160.
Sun, Boqin, et al.; "Core Analysis With Two Dimensional NMR"; SCA2002-38, pp. 1-12.
Sun, Boqin, et al.; "NMR Inversion Methods for Fluid Typing"; SPWLA 44$^{th}$ Annual Logging Symposium, Jun. 2003, pp. 1-12.
Sun, Boqin, et al.; "NMR Isotherm Studies of Gas Shales"; SPWLA 57$^{th}$ Annual Logging Symposium, Jun. 2016, pp. 1-14.
Wang, Hai-Jing, et al.; "High-Field Nuclear Magnetic Resonance Observation of Gas Shale Fracturing by Methane Gas"; Energy & Fuels, 2014, vol. 28, pp. 3638-3644.
Wang, Hai-Jing, et al.; "Water Adsorption in Nanoporous Carbon Characterized by in Situ NMR: Measurements of Pore Size and Pore Size Distribution"; 2014, The Journal of Physical Chemistry C, vol. 118, pp. 8474-8480.

* cited by examiner

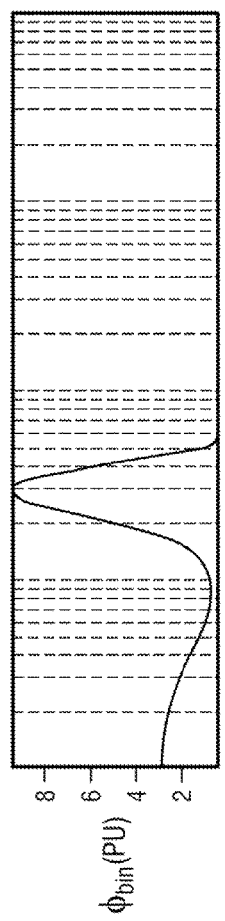
FIG. 4A
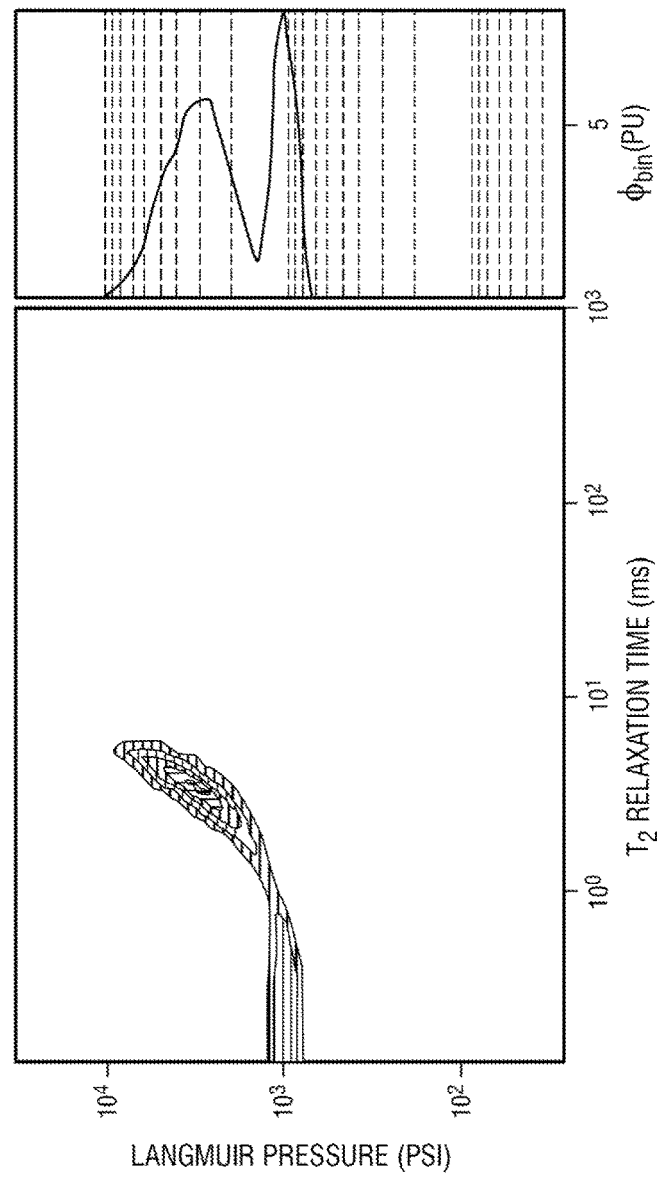
FIG. 4B
FIG. 4C

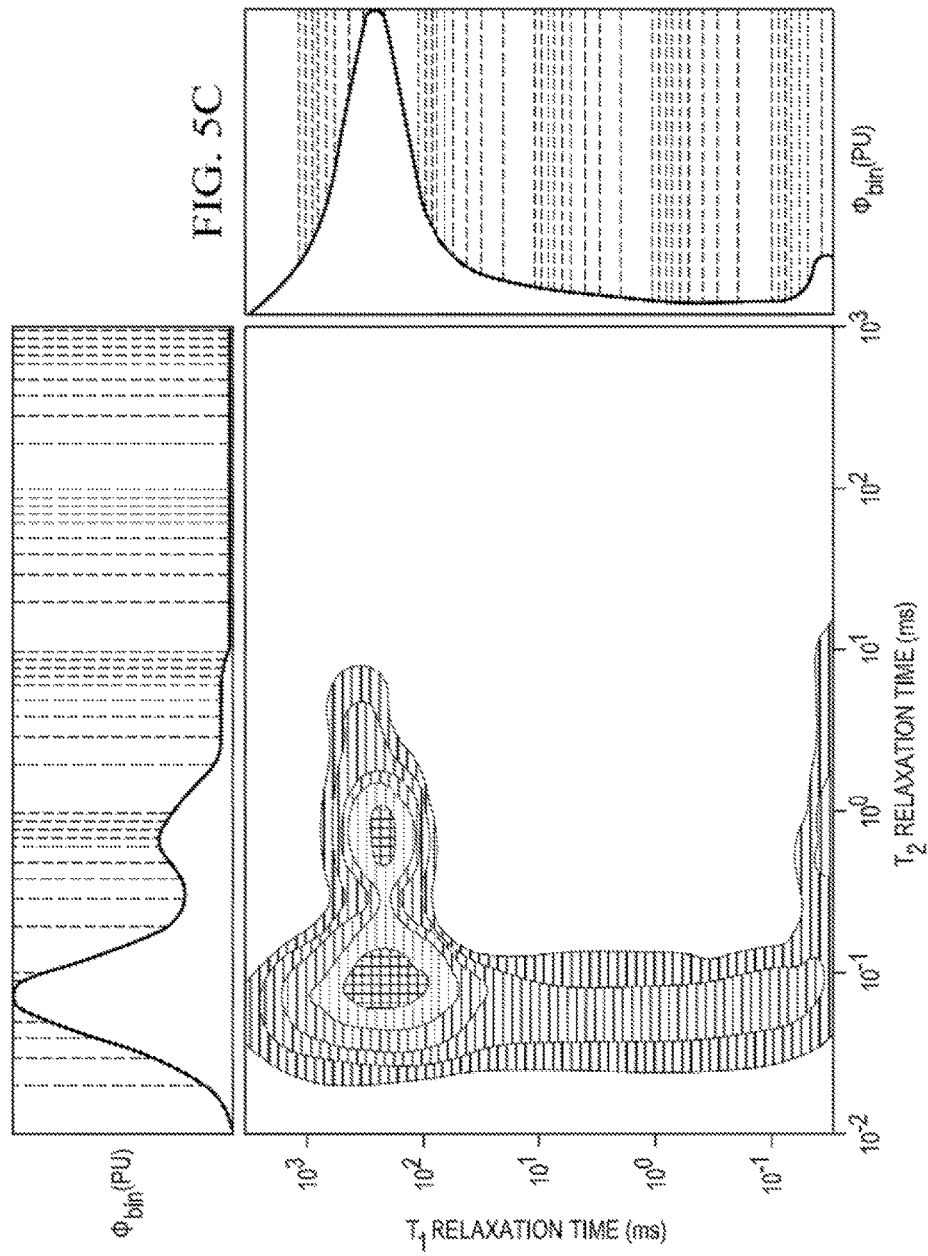

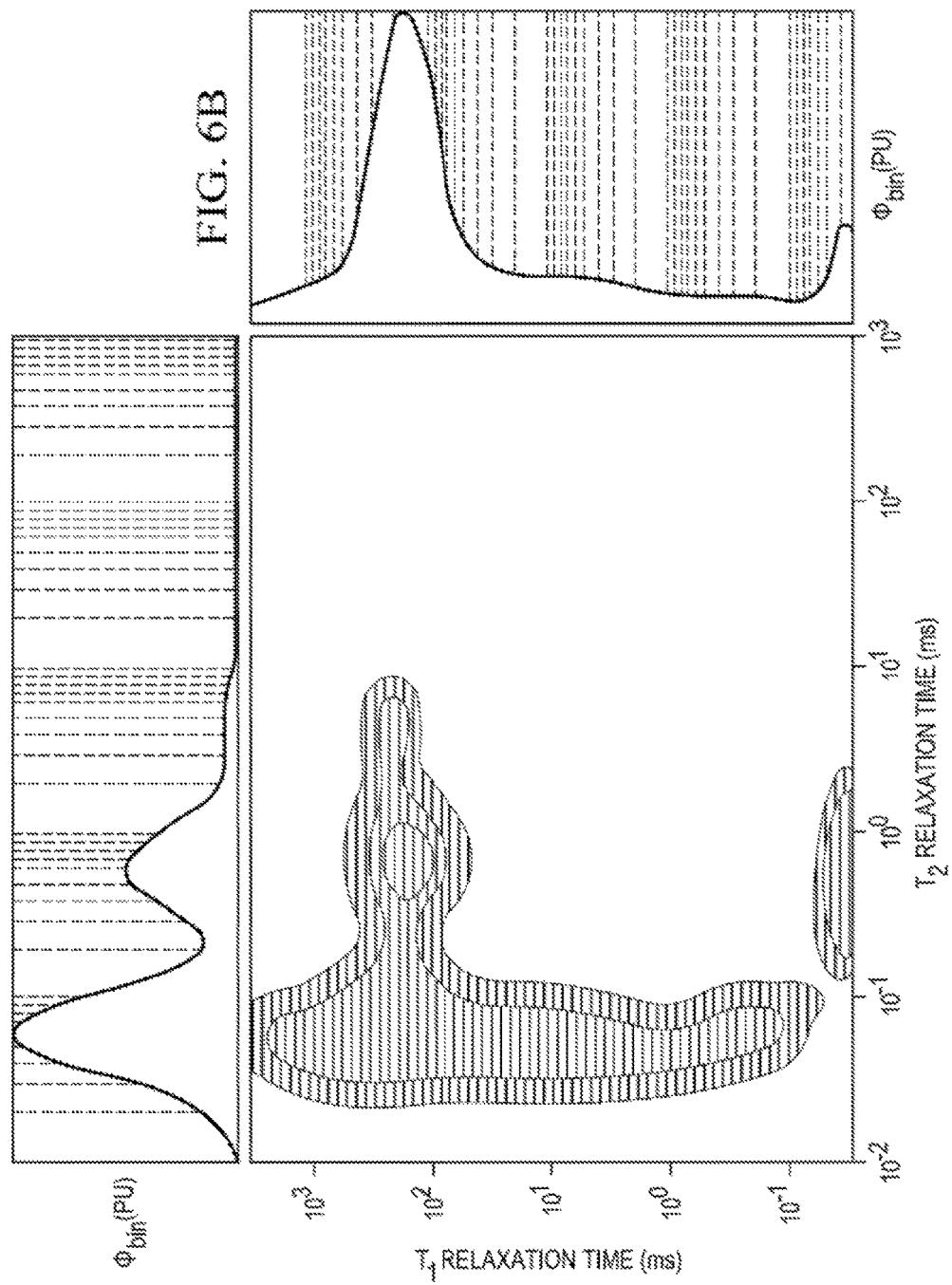

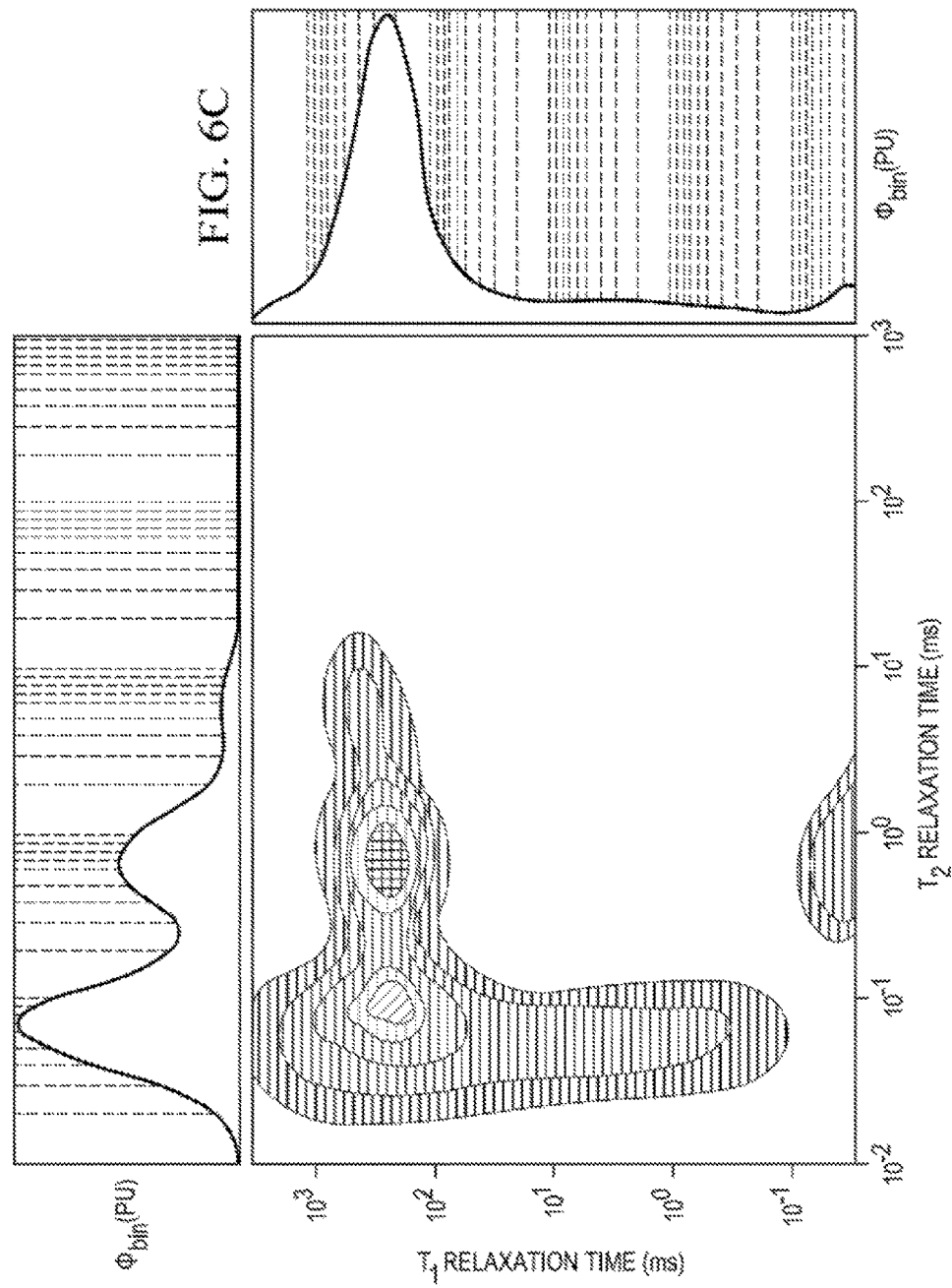

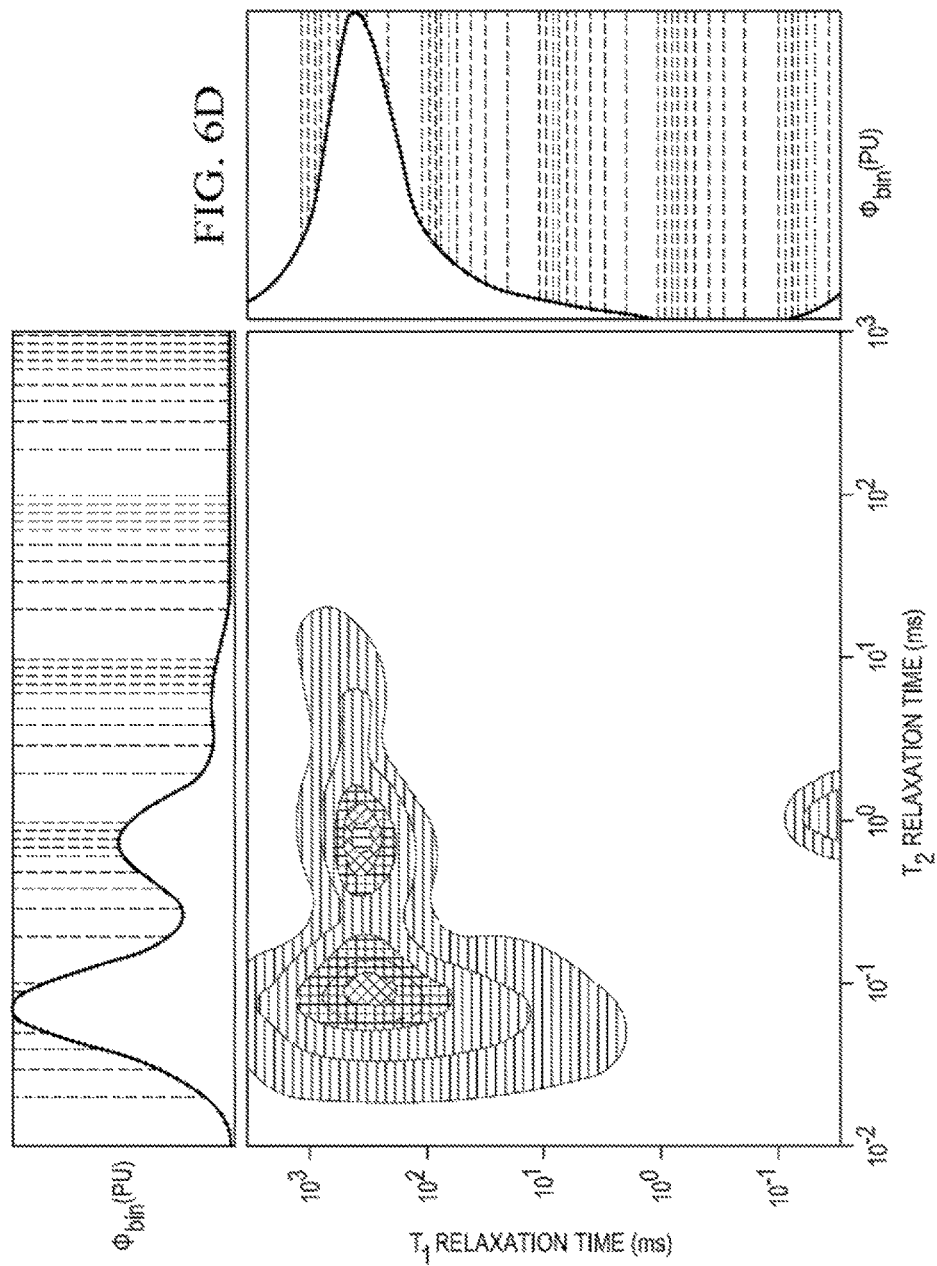

USING NMR RESPONSE DEPENDENCE ON GAS PRESSURE TO EVALUATE SHALE GAS STORAGE

BACKGROUND

Shale gas has become one of the most promising and fast-growing resources to supply the global energy needs in the foreseeable future. It is considered to be an unconventional resource because the gas is stored and "sealed" in pores of the source rock. The source rock typically has a low porosity (less than 10%) and an ultralow permeability (tens of nanodarcy), with significant amounts of the gas being stored in kerogen nanopores. To overcome the ultralow permeability and enable production of economic quantities of hydrocarbons, stimulation techniques such as hydraulic fracturing are usually required.

Unfortunately, shale gas storage mechanisms still remain poorly understood, often resulting in inaccurate estimation of original gas in-place (OGIP) within the reservoir. Existing laboratory techniques that were designed for use with conventional resources fail to provide accurate measurements for characterizing source rocks because of low permeability and porosity. Moreover, some of these techniques are destructive to the samples and others are very time consuming. For example, gas storage mechanisms can often be determined from adsorption isotherm measurements. These measurements are traditionally acquired using volumetric or gravimetric methods that have proven to be insensitive to the adsorbed or confined phase of gas in the nanometer-sized pores typical of shale. In general, these conventional techniques are unsuitable to meet the challenge of the current market needs.

SUMMARY

Accordingly, there is disclosed herein a method of characterizing gas adsorption on a rock sample that includes: (a) measuring a nuclear magnetic resonance (NMR) response of the rock sample as a function of surrounding gas pressure along an adsorption isotherm; (b) transforming the NMR response to obtain a Langmuir pressure distribution of gas adsorption on the rock sample; and (c) displaying the Langmuir pressure distribution. The Langmuir pressure distribution may be shown in one dimension (e.g., contribution to signal response versus Langmuir pressure), or may be combined with additional pressure-dependencies such as spin-lattice relaxation time ($T_1$), spin-spin relaxation time ($T_2$), and chemical shift ($\delta$) to form a multiple dimensional distribution. Some method embodiments further include: (d) identifying peaks in the Langmuir pressure distribution; and (e) associating a gas storage mechanism and capacity with each peak. Some method embodiments may still further include: (f) exposing the rock sample to a treatment fluid to obtain an altered sample; (g) repeating said measuring and transforming operations with the altered sample; and (h) comparing the Langmuir pressure distributions to determine effects of the treatment.

Further disclosed herein is a system for characterizing gas adsorption on a rock sample. The system includes a sample chamber containing the rock sample, a gas source, a probe, a processor module, and a user interface. The gas source pressurizes the sample chamber as the probe acquires measurements of an NMR response from the sample chamber as a function of gas pressure. The processor module transforms the measurements to obtain a Langmuir pressure distribution of gas adsorption on the rock sample. The user interface displays the Langmuir pressure distribution. Some embodiments of the system may further include a vacuum pump to evacuate ambient air and vapors from the sample chamber prior to pressurization. Each peak in the distribution may be associated with a gas storage component that indicates pore size or surface area, and may possibly further indicate the adsorption energy or chemistry of the adsorption surfaces.

BRIEF DESCRIPTION OF THE DRAWINGS

FIG. 4A is a graph of an illustrative $T_2$ distribution.

FIG. 4B is a graph of an illustrative two-dimensional Langmuir pressure-$T_2$ distribution.

FIG. 4C is a graph of a corresponding one-dimensional Langmuir pressure distribution.

FIGS. 5A-5E together show an illustrative three-dimensional Langmuir pressure-$T_1$-$T_2$ distribution of a dry sample.

FIG. 6A-6E together show an illustrative three-dimensional Langmuir pressure-$T_1$-$T_2$ distribution of a hydrated sample.

DETAILED DESCRIPTION

Herein, an NMR probe is combined with a high pressure gas loading system to provide a versatile and convenient alternative for adsorption isotherm measurements. NMR signal intensity is proportional to the total amount of NMR active nuclei enclosed in its sensitive detection coil, making measurements of the NMR signal response particularly suitable for quantifying the amount of adsorption. Moreover, NMR is able to differentiate different types of adsorbates (methane, ethane, propane, butane, etc.), and even different phases of the same adsorbate (e.g., adsorbed and confined phases), based on their respective unique NMR signatures including relaxation times. NMR relaxation times can also be used to understand the molecular dynamics and local environment of the nuclei. Thus the NMR-based measurement of multi-component adsorption isotherms enable novel understanding of gas storage mechanisms with microscopic details on the associated gas dynamics. This understanding is achievable even with shales and other rocks having very low porosity and permeability.

In the following discussion, ultrapure methane gas is employed as a good approximation to natural gas to pressurize the sample. Nevertheless, the disclosed method is also applicable to gas mixtures for adsorption measurement. Of particular interest are various components of natural gas and the combinations thereof, including the other gaseous alkanes (ethane, propane, butane, etc.), nitrogen, carbon dioxide, and hydrogen sulfide. To enhance their NMR signatures, nitrogen and carbon-oxide molecules may be isotopically enriched with $^{15}N$ and $^{13}C$, respectively. The NMR signal responses are measured at different gas pressures to construct the adsorption isotherm. The signal responses are then transformed to obtain a multi-dimensional distribution of the Langmuir adsorption and NMR relaxation parameters. Multi-dimensional cutoffs may then be applied to determine the gas adsorption parameters for different pore types. This approach efficiently overcomes the many challenges of shale gas storage analysis, including those attributable to microporosity and complex mineralogy.

Figure 1:
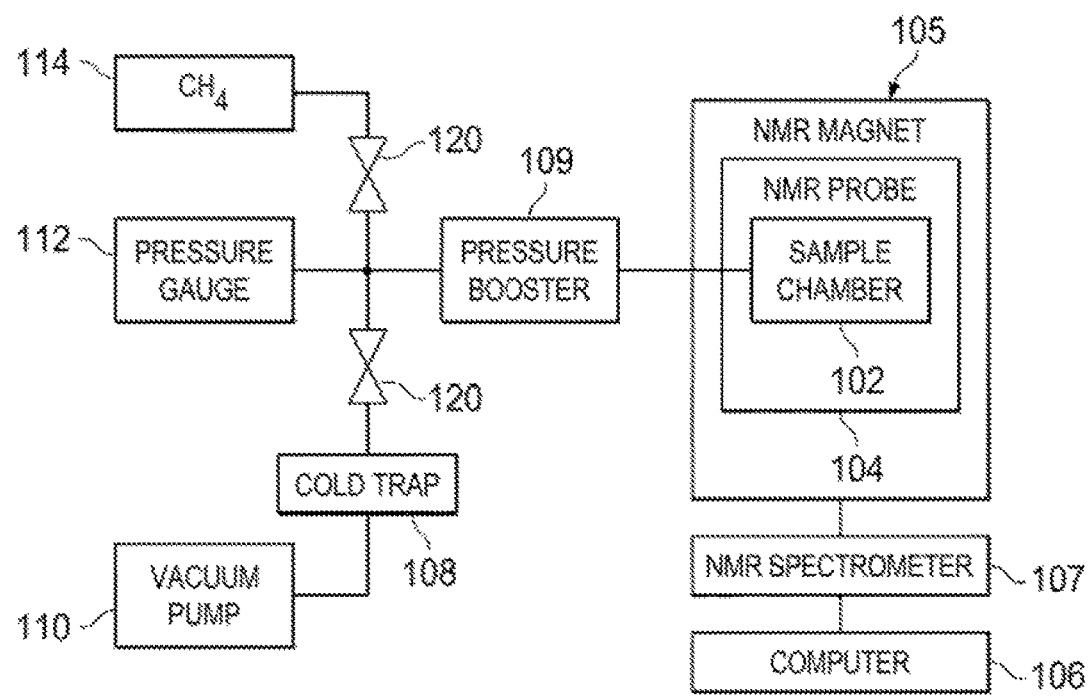
FIG. 1 is a block diagram of an illustrative rock sample characterization system.

FIG. 1 shows an illustrative rock sample characterization system having a pressurizable sample chamber 102 enclosed within the coils of an NMR probe 104 (e.g., a standard Bruker 5 mm probe) placed inside an NMR magnet 105. A processor module 106, typically in the form of a computer configured with a suitable data-acquisition interface (e.g., NMR spectrometer 107) and corresponding software, controls the NMR probe 104 to acquire measurements of the NMR signal responses as a function of gas pressure and to process those responses in accordance with the methods outlined below. The sample chamber 102 is further coupled via a cold trap 108 with a vacuum pump 110 to evacuate unwanted air and vapor from the sample chamber 102 prior to injection of the pressurizing gas. (The intermediate pressure booster 109 has a bypass to permit the evacuation.) A pressure gauge 112 enables the sample chamber pressure to be monitored during the evacuation process and the subsequent pressurization process.

A gas source 114 provides gas for pressurizing the sample chamber 102. One contemplated system employs a high pressure cylinder of high purity methane gas (99.999% research grade, available from Airgas) coupled to pressure booster 109, which includes a high pressure generator and a syringe pump to boost the achievable gas pressures in the sample chamber 102. Together, the source and pressure booster enable the system to provide gas pressures of 12 kpsi or more. A series of manual valves 120 enables the source 114, or cold trap 108 and vacuum 110, to be selectively coupled to the sample chamber 102, and further enables the sample chamber to be decoupled entirely from both the source 114 and vacuum 110, as needed to enable loading of the sample chamber, evacuation of the sample chamber, pressurization of the sample chamber, and venting of the sample chamber.

The experimental results discussed below were obtained by loading the gas shale samples in a high pressure NMR sample tube, which was then placed inside a high field NMR spectrometer that operated at 500 MHz $^1$H NMR frequency (Bruker). Although the embodiments described herein are discussed within the context of low permeability rocks such as shale, it is contemplated that the methods and systems disclosed may be used in conjunction with any type of rock samples. Methane and other hydrocarbon gases contain protons that carry NMR active nuclei, $^1$H with nuclear spin-1/2, enabling them to be detected by $^1$H NMR probe frequencies using any of the well-known NMR parameter acquisition techniques, in turn enabling the NMR probe to measure gas adsorption in a shale sample as a function of gas pressure.

One technique measures NMR signal responses stimulated by a single radio frequency (RF) pulse corresponding to a spin flipping angle of π/2. This NMR signal response is known as Free-Induction-Decay (FID). The FID can be Fourier-transformed and processed into NMR spectra. The integrated area under the NMR peak is proportional to the total amount of gas within detection region. If desired, the central frequency and linewidth of the NMR peak can be used to identify gas in different phases, different molecular dynamics, and different local environments. Depending on the substance and its local environment, the central frequency can exhibit a chemical shift, Knight shift, or nucleus independent chemical shift.

Another technique measures the spin-lattice relaxation time ($T_1$), a parameter characterizing how fast the longitudinal spin magnetization can relax back to the thermal equilibrium, using an inversion recovery sequence (e.g., a π pulse followed by a π/2 pulse of the same phase) or any version of saturation recovery sequence. $T_1$ is sensitive to the molecular exchange between surface adsorbed and pore space confined gas. The adsorbed gas has shorter $T_1$ because of the restricted motion on the surface. The $T_1$ of confined gas is a weighted average of $T_1$ of free gas and adsorbed gas depending on how fast the exchange between two phases.

Yet another useful technique measures the spin-spin relaxation time ($T_2$), a parameter characterizing how fast the transverse spin magnetization can relax to zero upon interactions with neighboring spins or local environment, using a pulse-echo sequence such as Hahn Echo and Carr-Purcell-Meiboom-Gill (CPMG) sequences. In the Hahn echo sequence, a (π/2)x-pulse is followed by a (π)y-pulse at the time τ after the initial (π/2)x-pulse to refocus the NMR signal at 2τ (x and y here indicate their relative phase of the pulse). As with other pulse-echo sequences, the signal is better preserved, i.e., it is not cut off by the detection delay resulting from the intrinsic characteristics of the NMR resonant circuits. The CPMG sequence consists of a train of π-pulses with alternating phases to repeatedly and dynamically refocus NMR signal. It can compensate for the fast signal decay due to molecular diffusion and achieve much higher signal-to-noise ratio. $T_2$ is sensitive to the translational motion of gas molecules and local magnetic field gradient.

$T_1$ and $T_2$ provide additional dimensions in NMR spectroscopy for accurate quantification of gas molecules within detection region and for precise differentiation of gas molecules in different phases, molecular dynamics, and local environments. The selected NMR measurements were repeated at each pressure step as the gas pressure was increased stepwise until reaching a preset limit (e.g., the elevated reservoir pressure). The adsorption process was closely monitored by observing the change in NMR signal intensity, frequency shift, linewidth, $T_1$, and $T_2$, as the function of the gas pressure. We conclude that these measurement parameters reveal not only the gas storage mechanisms by separating the adsorbed gas from confined or free gas, but also the gas storage capacity of each mechanism.

Laplace transform algorithms are used to process adsorption and NMR data to obtain multi-dimensional distribution of Langmuir adsorption and NMR relaxation parameters, which contain the key information regarding the microporosity and gas storage mechanism. Conventionally, the Laplace transform is applied to the dependence of the NMR signal response on the adjustable parameters of an NMR pulse sequence, such as spacing time between pulses and applied magnetic field gradient, to obtain the distribution of $T_1$, $T_2$, and diffusion coefficient. The transform process is further extended here with an inverse Laplace transform to analyze the dependence of the NMR signal response on gas pressure. Whether analyzed in terms of pressure dependence alone or in combination with the other spectroscopic information, the NMR-based isotherm measurements reveal valuable information about the distribution of pore volumes and surface chemistry.

Adsorption isotherms may demonstrate a variety of shapes and patterns, depending on the characteristics of both adsorbate and adsorbent, such as the surface adsorption energy, the number of available adsorption sites, the pore size and its distribution. They are classified into six types according to the IUPAC recommendations (see Sing, K., et al. (1985). Reporting Physisorption Data for Gas Solid Systems with Special Reference to the Determination of Surface-Area and Porosity (Recommendations 1984). Pure Appl. Chem., 57, 603-619). Each isotherm type is governed by certain adsorption mechanism and isotherm equation associated with it. The essential parameters related to adsorption can be determined using the appropriate equations to fit and analyze the adsorption isotherms. These equations serve as the basis for the extended transform mentioned above.

Adsorption isotherms of methane gas in gas shale have been measured. They show common characteristics of a Langmuir adsorption (type I isotherm) plus a linear component, which can be described as:

$$V_i = V_c P_i + V_L \frac{P_i/P_L}{1 + P_i/P_L}$$

where $P_i$ is the pressure and $V_i$ is the measured quantity at $P_i$, $V_c$ is the amount of gas that is confined in the pores, $V_L$ and $P_L$ are Langmuir volume and Langmuir pressure parameters that are indicative of the number of surface adsorption sites and the adsorption energy.

However, this classical treatment, termed as Langmuir Adsorption Isotherm (LAI), is unsuitable for processing adsorption data that involve multiple Langmuir adsorption components, which is very common in heterogeneous porous media with a distribution of pore size and adsorption energy. As shale typically includes both organic and inorganic pores in a wide array of pore size and surface chemistry in gas shale, we generalize the foregoing isotherm equation to include multiple Langmuir adsorption terms in the isotherm equation:

$$V_i = V_c P_i + \sum_j V_{L,j} \frac{P_i/P_{L,j}}{1 + P_i/P_{L,j}}$$

where $V_{L,j}$ and $P_{L,j}$ are Langmuir volume and pressure of the jth component. Because this equation allows for a distribution of Langmuir pressures, this approach is herein termed as the Isothermal Langmuir Adsorption Pressure (ILAP) distribution method.

Curve fitting of the generalized equation to the measured adsorption isotherms is possible, but generally requires some knowledge of the number and volume for each Langmuir components. To circumvent this issue, we note that the generalized equation is amenable to decomposition via an inverse Laplace transform. In other words, by applying an inverse Laplace transform to the measured adsorption isotherm, one obtains a Langmuir pressure distribution without having to know the shale porosity or having to assume surface homogeneity, providing a simplified analysis on adsorption data and accurate quantification of storage capacity for each type of adsorption energy and pore size.

Figure 2A:
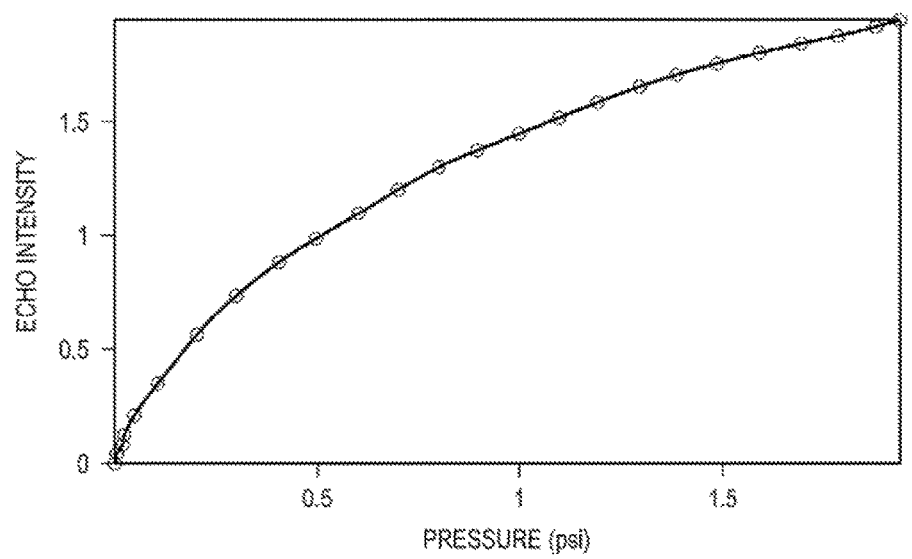
FIG. 2A is a graph of an adsorption isotherm of an untreated sample.
Figure 2B:
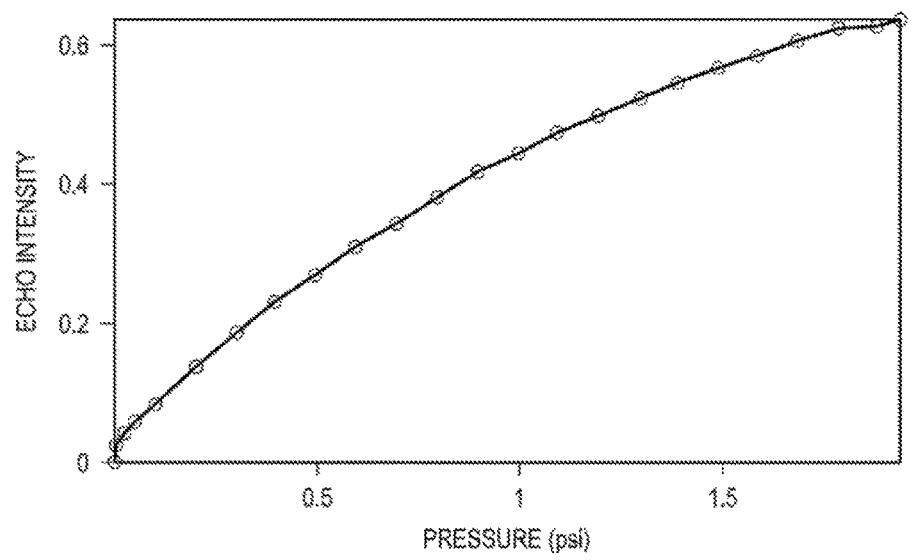
FIG. 2B is a graph of an adsorption isotherm of a bleached sample.
Figure 3A:
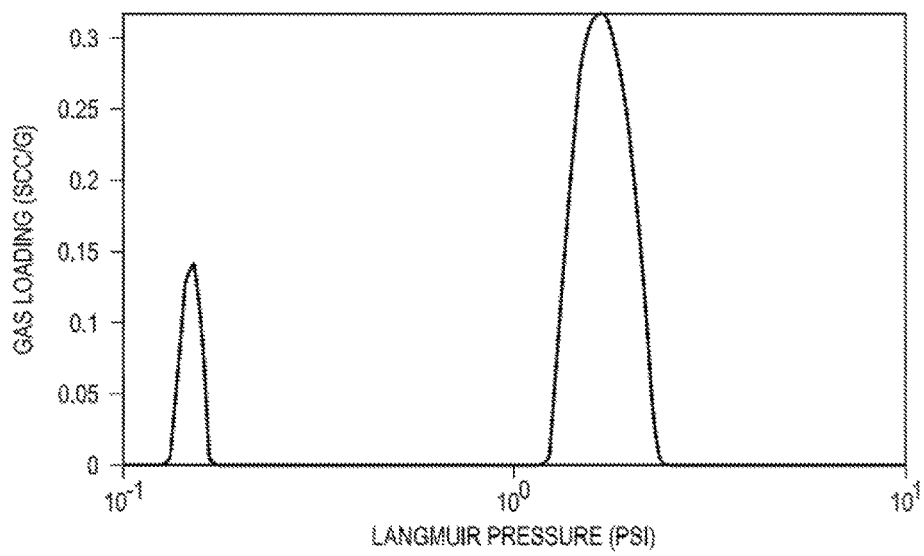
FIG. 3A is a graph of a Langmuir pressure distribution for the untreated sample.
Figure 3B:
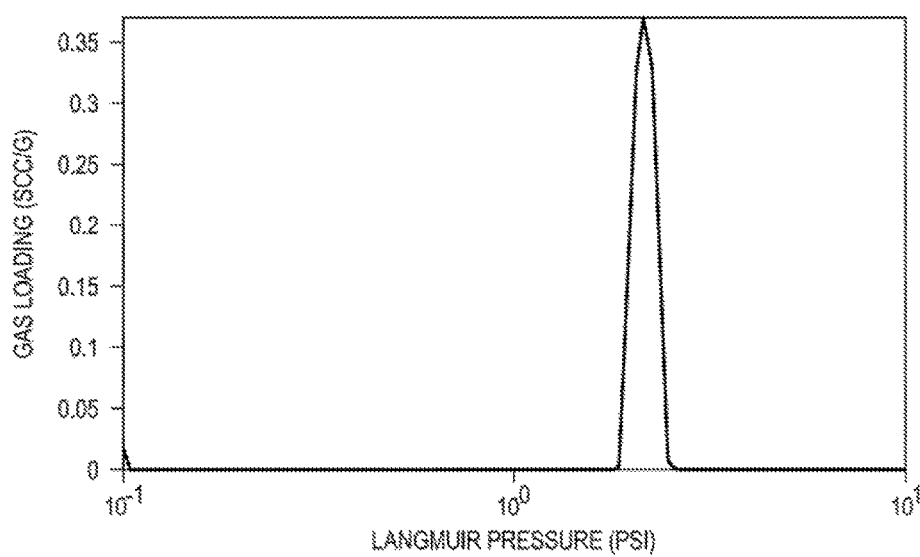
FIG. 3B is a graph of a Langmuir pressure distribution for the bleached sample.
Figure 5A:
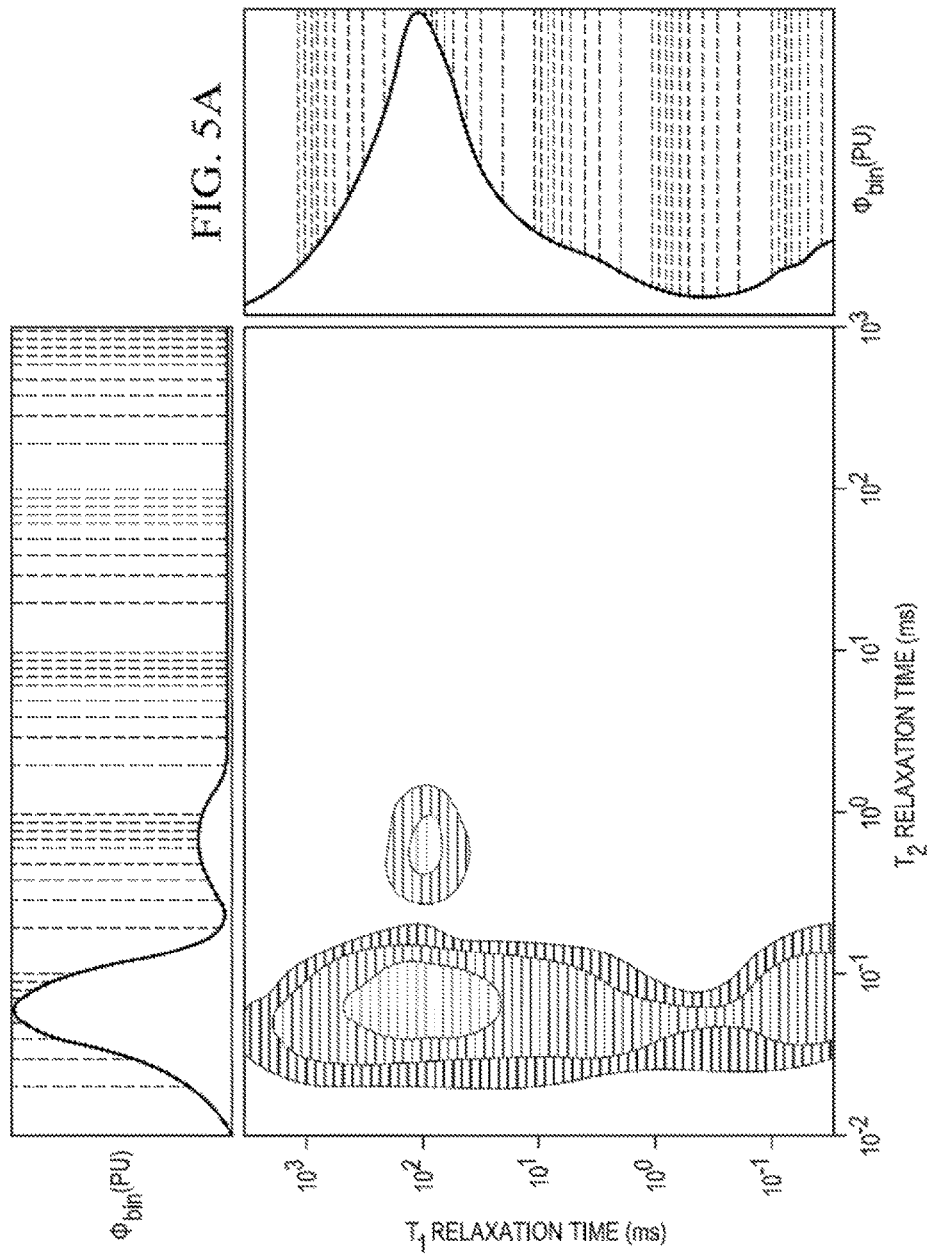
Figure 5B:
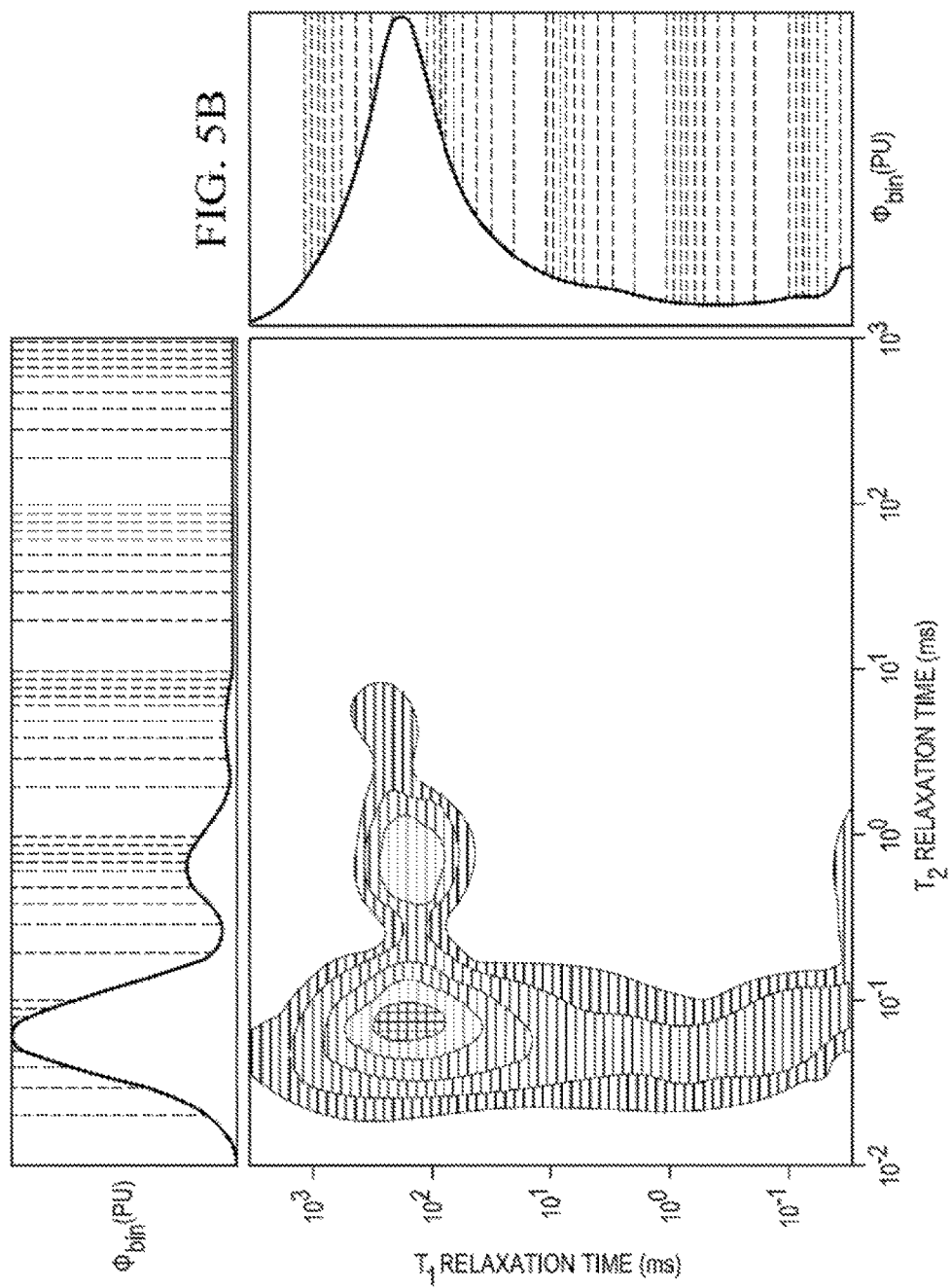
Figure 5D:
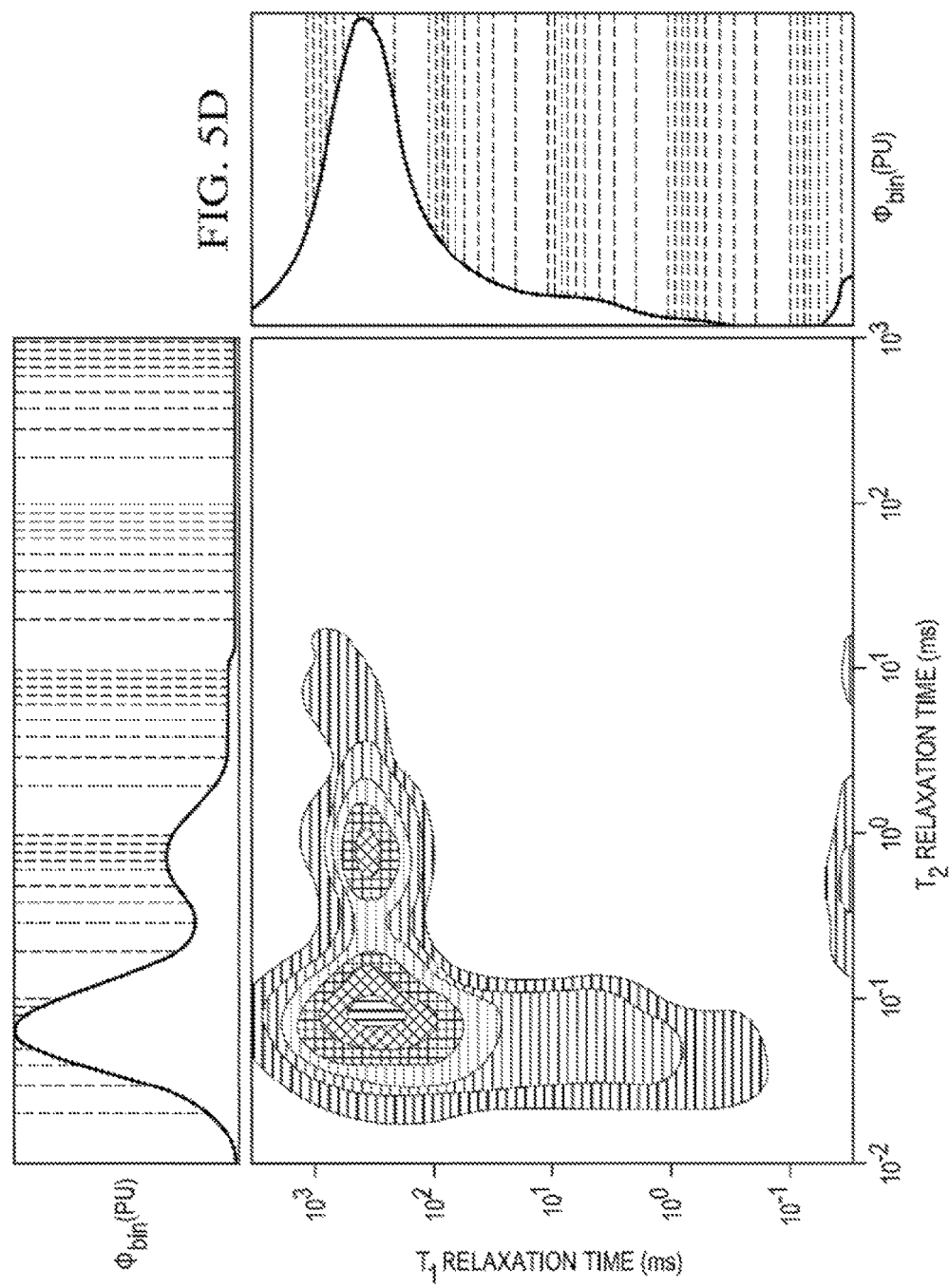
Figure 5E:
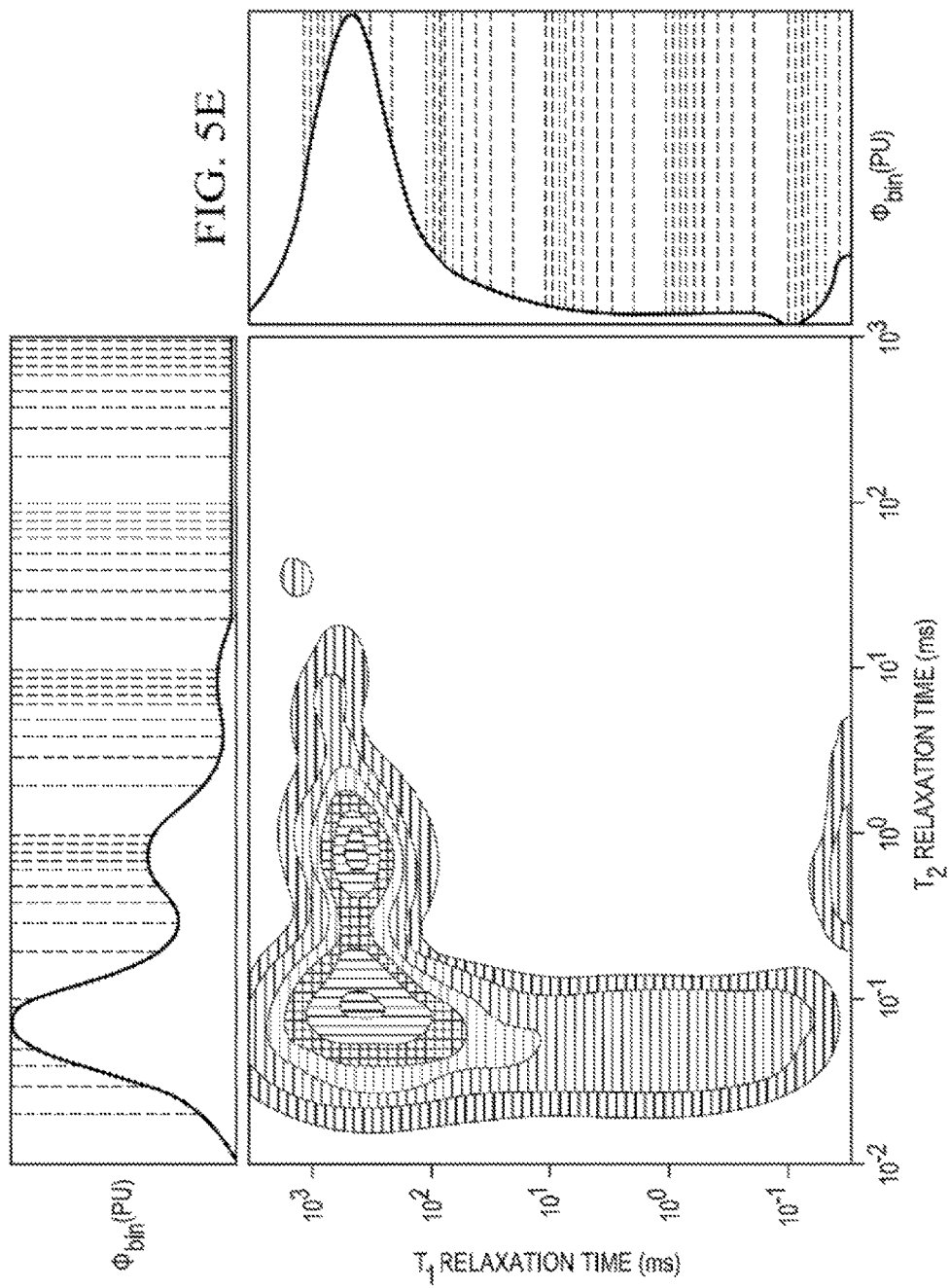
Figure 6A:
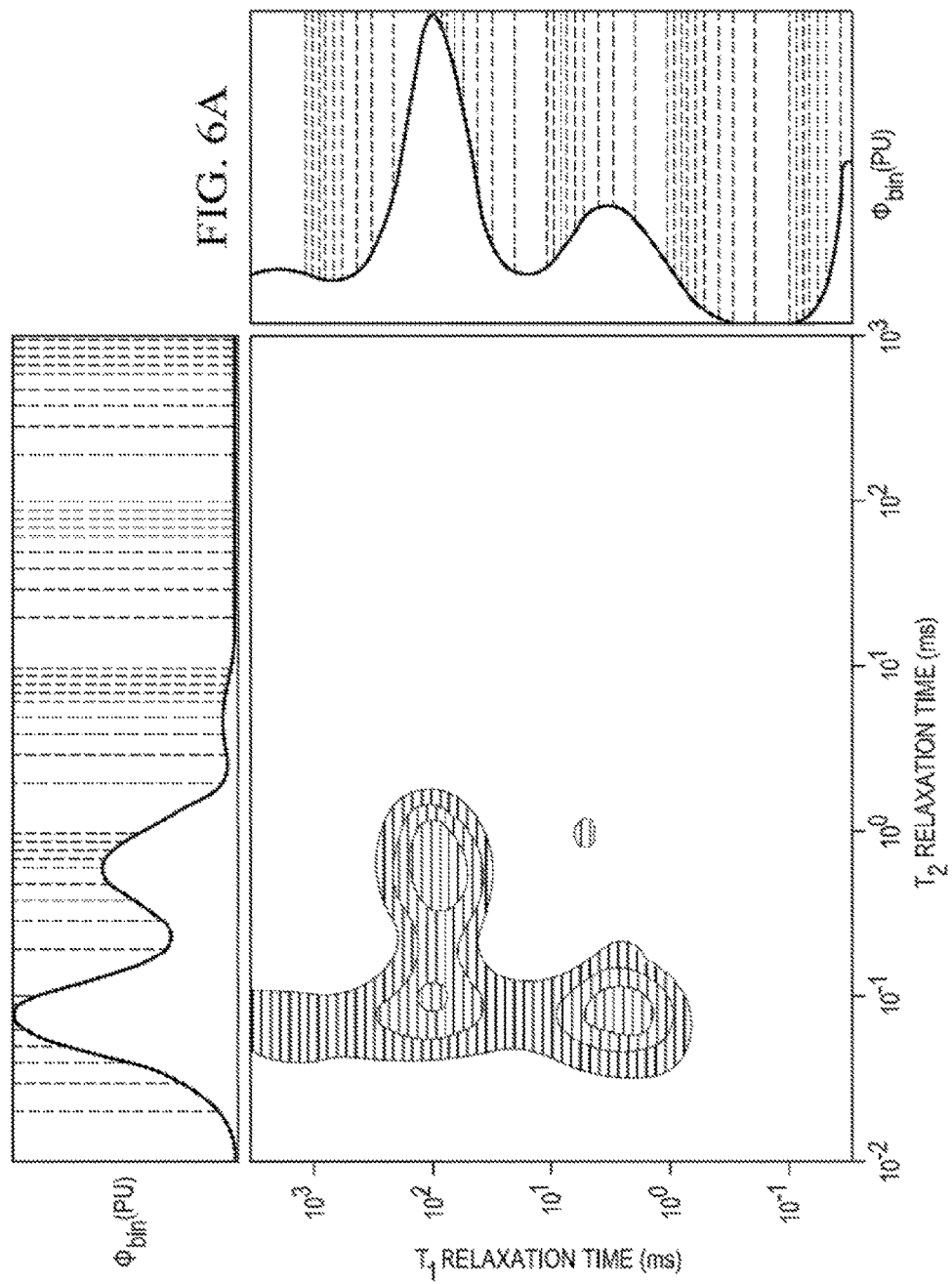
Figure 6E:
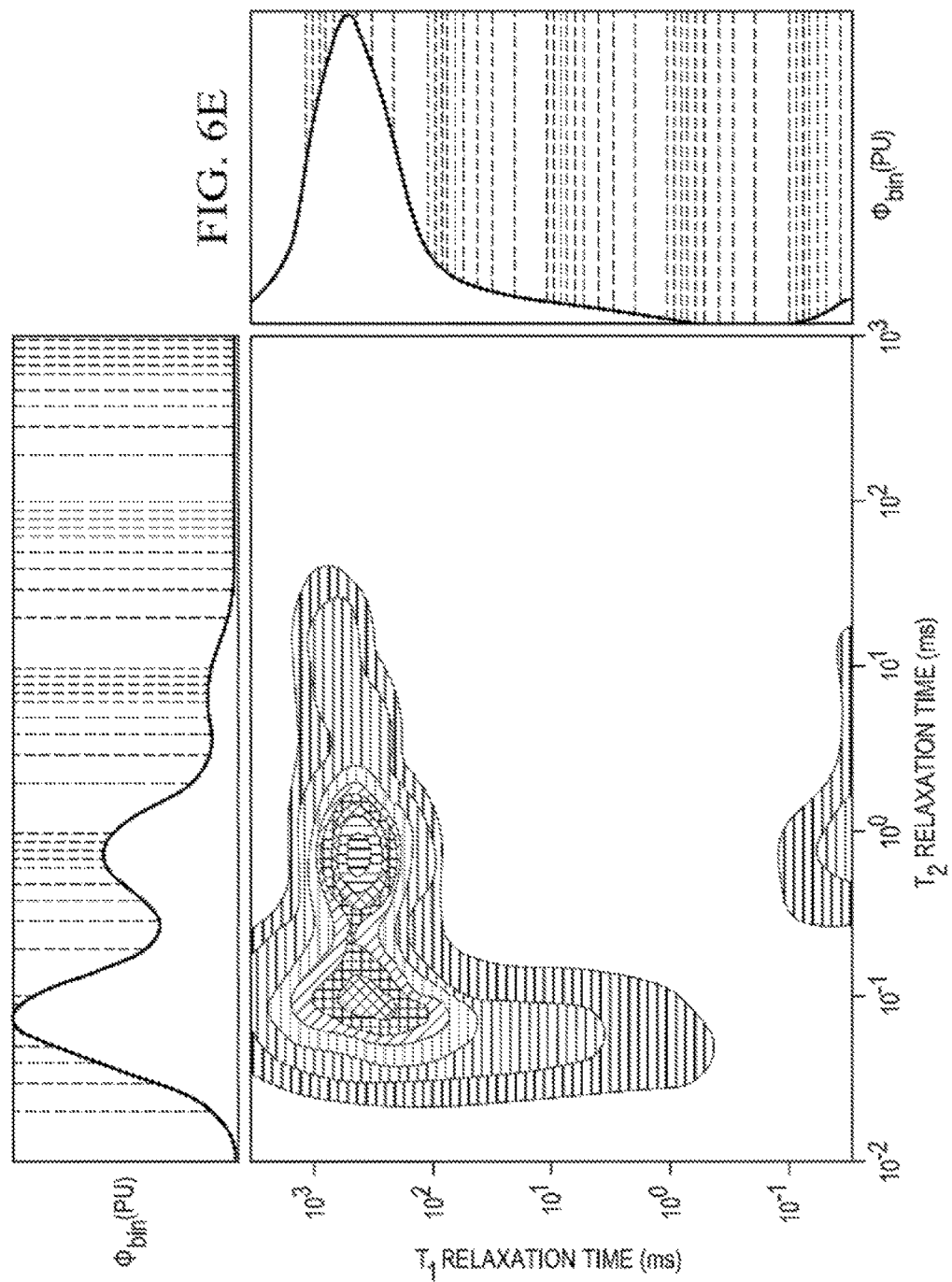

Consider the adsorption isotherm of FIG. 2A showing the gas adsorption as a function of gas pressure for an untreated shale sample. Applying an inverse Laplace transform yields the ILAP distribution of FIG. 3A, shown as a graph of gas loading (in standard cubic centimeters per gram of matrix material) versus Langmuir pressure. The distribution reveals two clearly separated peaks; one at about $P_L$=0.15 psi and one at about $P_L$=1.7 psi. The sample was then bleached to remove kerogen and other organic material. The new isotherm measurement is shown in FIG. 2B and the new ILAP distribution is shown in FIG. 3B having a single peak at about $P_L$=2.1 psi. The disappearance of the first peak indicates that it represented pores in the organic material, which had a stronger attraction for methane. This is deducible because the peak related to organic pores has smaller Langmuir pressure (i.e., a stronger binding energy). We note that the ILAP distribution method disclosed herein is not limited to NMR-measured adsorption isotherms, but rather it is also applicable to adsorption isotherms measured by non-NMR methods including the volumetric or gravimetric methods suitable for higher-porosity materials.

Additional dimensions for the distribution can be derived by extracting traditional NMR parameters from the NMR response signals to yield, e.g., a multi-dimensional distribution of Langmuir pressure and NMR relaxation time. Such a multi-dimensional ILAP distribution is useful because NMR relaxation and diffusion phenomena all depend on pressure. The dependency is useful to identify the different phases of methane molecules when confined in or adsorbed on shale. In particular, Laplace transform techniques are already used to extract both $T_1$ and $T_2$ from NMR response signals. Langmuir pressure distribution can be combined with either or both of $T_1$ and $T_2$ distribution to form a multi-dimensional ILAP distribution map. As Laplace transforms are linear, the order in which the transforms are performed is generally interchangeable. Moreover, the close relationship between a Laplace transform and the inverse Laplace transform allows them to be considered equivalent in the present context.

If we combine the ILAP distribution method with a determination of the $T_2$ distribution, for example by using a 2-dimensional Laplace transform algorithm, we obtain a two-dimensional ILAP-$T_2$ distribution map such as that shown in FIG. 4B. FIG. 4B uses color, shading, or contours to represent the spectral component contribution to the NMR signals as a function of Langmuir pressure and $T_2$ relaxation time. FIG. 4A shows the one-dimensional $T_2$ distribution (obtainable by integrating FIG. 4B over Langmuir pressure), while FIG. 4C shows the one-dimensional $P_L$ distribution. In each of these views, two separate peaks are visible, and the two-dimensional map shows the characteristic $P_L$ and $T_2$ (ranges) associated with each peak. Based on the fact that the $T_2$ of gas is shorter in smaller pores due to the higher surface-to-volume ratio, the peak with shorter and lower Langmuir pressure in ILAP-$T_2$ maps can be assigned to gas adsorption in small pores, while the peak with longer $T_2$ and higher Langmuir pressure is assigned to gas adsorption in large pores. Thus, the 2D ILAP-$T_2$ distribution map can be used to further differentiate adsorbed gas according to pore size, with smaller $T_2$ indicating smaller pores. This map may be particularly useful for tracking adsorption progress by in situ monitoring of peak growth and shift associated with each gas component shown in the ILAP-$T_2$ map. Furthermore, the ILAP distribution method can be combined with 2D $T_1$-$T_2$ NMR measurement to generate 3D ILAP-$T_1$-$T_2$ distribution maps.

FIGS. 5A-5E show 2D NMR $T_1$-$T_2$ distribution maps as a function of gas pressure for a dry shale sample at 100, 250, 500, 750, and 1000 psi, respectively. FIGS. 6A-6E show the corresponding maps for the shale sample that has been hydrated prior to gas adsorption. Each map is accompanied by a panel showing the (normalized) overall $T_1$ distribution and a panel showing the (normalized) overall $T_2$ distribution for that pressure point. In the dry shale sample (FIGS. 5A-5E), two peaks appear at about $T_2$=0.06 and 0.6 millisecond (ms). The intensity of the peak at $T_2$=0.06 ms reaches saturation at around 750 psi, corresponding to the Langmuir adsorption behavior for gas in small pores. The peak at $T_2$=0.6 ms keeps growing as pressure increases, corresponding to the confined gas increasing linearly with pressure. In the hydrated sample (FIGS. 6A-6E), the peak at about $T_2$=0.06 is assigned to hydration water, which doesn't respond to increasing methane pressure. The two peaks at about $T_2$=0.6 and 20 represent gas confined in large pores and in between granules, respectively. The comparison of dry and hydrated shale sample suggests that the smaller pores are preferentially occupied (and blocked against methane adsorption) by the water molecules.

The Langmuir pressure distribution is not explicitly shown in FIGS. 5-6, but can be readily obtained using the inverse Laplace transform as outlined previously. Such further analysis has revealed that gas adsorption in nanopores demonstrates Langmuir adsorption behavior, and that gas adsorption in larger pores demonstrates normal gas storage mechanism with linear dependence on pressure. These examples suggest that the 3D ILAP-$T_1$-$T_2$ distribution map provides additional dimension and resolution, enabling NMR to further differentiate multi-component gas adsorbates, such as a mixture of methane and water vapor, in a variety of adsorbed/confined phases and pore sizes. The 3D ILAP-$T_1$-$T_2$ distribution can thus be used for multi-component adsorption study in gas shale, such as a gas mixture with composition similar to that in the reservoir for accurate simulation of phase behavior.

The same principle can be applied to chemical shift and other NMR shift due to the local magnetic environment, such as the nucleus independent chemical shift. The chemical shift, often labelled as δ, can be identified when molecules undergo fast motion in liquid or gaseous phases. The chemical shift and relative intensity of each individual peaks in NMR spectra are often diagnostic of the molecular structure. For instance, methane gas has one $^1$H peak for all four equivalent protons in CH4. For butane (CH3-CH2-CH2-CH3), the proton chemical shift in —CH3 groups are well separated from those in —CH2 groups. Thus chemical shift can be used to concurrently analyze multiple components in hydrocarbon mixtures. NMR peaks may be further shifted by other mechanisms such as local magnetic susceptibility. As a pressure dependent measurement, the chemical shift provides a unique and diagnostic chemical identifier for multi-component gas mixtures and their respective distribution among adsorbed/confined phase in porous media. Combing the adsorption isotherm and chemical shift, one can obtain a 2D ILAP-δ distribution map using the inverse Laplace transform. It can be further combined with $T_1$ and $T_2$ to form 4D distribution maps.

Here, we have applied multi-dimensional cutoffs to interpret gas adsorption parameters and quantify gas storage capacities for different pore sizes and adsorbed/confined phases. The multi-dimensional distribution of adsorption energy and NMR relaxation time generated by Laplace inversion algorithm is an indicative of gas molecules in various phases and local environment, such as gas adsorbed on pore surface, confined in nano- to micro-pores, and in meso- to macro-pores. The established NMR relaxation mechanism can be used to qualitatively assign certain area of the multi-dimensional distribution to gas in certain phase and type of pore size. Multi-dimensional cutoffs provide the quantitative threshold values/lines that separate those areas, allowing gas in each phase and type of pore sizes to be computationally separated and quantified using the integrated volume under the distribution map. The choice of multi-dimensional cutoffs is usually chosen as the minimum values between two peaks, but other cutoff selection strategies can be employed.

Figure 7:
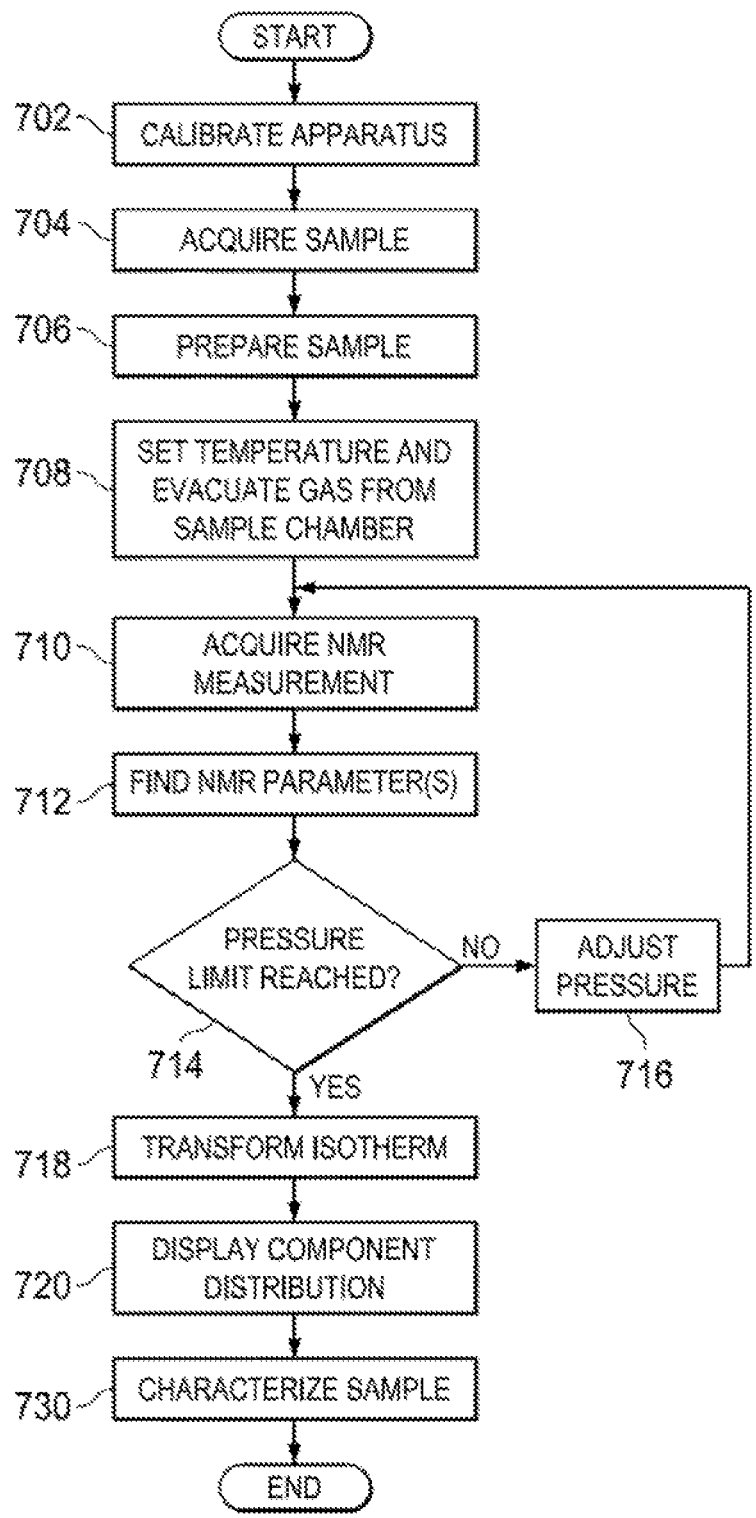
FIG. 7 is a flow chart of an illustrative rock sample characterization method.

FIG. 7 is a flow diagram of one illustrative method embodiment. It begins in block 702 with a calibration operation to determine the NMR signal response intensity for each of multiple adsorbate concentrations in the sensing region. In block 704, the rock sample is acquired and optionally homogenized by grinding and screening out any particles above a given size. In block 706 the sample is prepared, which includes performing any desired pre-treatments such as dehydration, bleaching, etc. Block 706 further includes placing the sample in the NMR probe sample chamber.

In block 708, the system sets the temperature, which will be maintained throughout the isotherm measurement process. Moreover, it has been observed that the present method is not particularly temperature sensitive, enabling the measurements to be acquired relatively fast even in the absence of a thermal bath. Nevertheless, there are expected to be benefits for quantifying adsorption behavior at reservoir temperatures, and some system embodiments are equipped with a heating device and maintaining the temperature of the sample chamber. Block 708 further includes evacuating air and vapor from the sample chamber in preparation for the pressurization step.

In block 710, the system measures the pressure and the associated NMR signal response, preferably measuring the signal amplitude as a function of pulse spacing and other NMR measurement parameters that may reveal additional information about the local environment for the $^1$H nuclei. In block 712, the desired NMR parameter(s) (e.g., $T_1$ and $T_2$ distributions) are extracted. In block 714, the system determines whether the predetermined pressure limit has been reached. If not, the system adjusts the sample chamber pressure, e.g., by adding more pressurization gas, in block 716 before returning to block 710.

Blocks 710-716 are repeated until the predetermined pressure limit has been reached, at which point the system reaches block 718. In block 718, the processing module calculates an inverse Laplace transformation of the NMR signal's dependence on pressure (or of the extracted NMR parameters' dependence on pressure) to obtain a Langmuir pressure distribution having one or more dimensions. This distribution is displayed in block 720 to a user.

The displayed distribution is preferably provided to the user via an interactive user interface. Whether based on input from the user or based on an automated process, the system characterizes the sample in block 730. Such characterization may include identifying any peaks in the distribution, identifying Langmuir pressures and other parameter values associated with the peaks, and associating each peak with a storage mechanism. Such storage mechanisms may be specified in terms of pore size, surface chemistry, and phase status.

The foregoing process can be extended to include new storage mechanisms as they are recognized. For example, some heavier hydrocarbons such as butane, propane, and hexane, may exhibit a capillary condensation effect in shale. The pressurizing gas may be modified to include some of these heavier hydrocarbons to reveal the extent of this storage mechanism.

Based on the results of the foregoing characterizations, reservoir engineers may be able to better evaluate the reservoir. For example, a precise understanding of the gas storage mechanism and its capacity provide inputs for an accurate estimation of OGIP and the recoverable quantity. This is particularly important for reservoirs containing wet gas or retrograde condensate, as several gas storage mechanisms are involved at the same time.

Numerous other modifications, equivalents, and alternatives, will become apparent to those skilled in the art once the above disclosure is fully appreciated. It is intended that the following claims be interpreted to embrace all such modifications, equivalents, and alternatives where applicable.

What is claimed is:

1. A method for characterizing gas adsorption of a rock sample that comprises:
    (a) measuring a nuclear magnetic resonance (NMR) response of the rock sample as a function of a surrounding gas pressure along an isotherm;
    (b) transforming the NMR response to obtain a Langmuir pressure distribution of gas adsorption on the rock sample; and
    (c) displaying the Langmuir pressure distribution so as to characterize gas adsorption from the rock sample.

2. The method of claim 1, wherein the Langmuir pressure distribution is displayed as a response intensity contribution as a function of Langmuir pressure.

3. The method of claim 1, wherein the Langmuir pressure distribution is displayed as a response intensity contribution as a function of Langmuir pressure and spin-lattice relaxation time ($T_1$).

4. The method of claim 1, wherein the Langmuir pressure distribution is displayed as a response intensity contribution as a function of Langmuir pressure and spin-spin relaxation time ($T_2$).

5. The method of claim 1, wherein the Langmuir pressure distribution is displayed as a response intensity contribution as a function of Langmuir pressure and chemical shift ($\delta$).

6. The method of claim 1, wherein the Langmuir pressure distribution is displayed as a response intensity contribution as a function of Langmuir pressure and any two or more of: spin-lattice relaxation time ($T_1$), spin-spin relaxation time ($T_2$), and chemical shift ($\delta$).

7. The method of claim 1, further comprising:
    (d) identifying peaks in the Langmuir pressure distribution; and
    (e) associating a gas storage mechanism and capacity with each peak.

8. The method of claim 7, wherein the gas storage mechanism is indicative of a pore size or pore surface area.

9. The method of claim 8, wherein the gas storage mechanism is further indicative of an adsorption energy.

10. The method of claim 7, further comprising:
    (f) exposing the rock sample to a treatment fluid to obtain an altered sample;
    (g) repeating said measuring and transforming operations with the altered sample; and
    (h) comparing the Langmuir pressure distributions to determine effects of the treatment.

11. The method of claim 1, wherein said measuring includes modifying the pressure by supplying one or more components of natural gas to a sample chamber containing the sample.

12. The method of claim 11, wherein said one or more components comprise methane or at least one other gaseous alkane.

13. The method of claim 11, wherein said one or more components comprise hydrogen sulfide.

14. The method of claim 11, wherein said one or more components comprise nitrogen isotopically enriched with $^{15}N$.

15. The method of claim 11, wherein said one or more components comprise carbon monoxide or carbon dioxide isotopically enriched with $^{13}C$.

16. The method of claim 1, wherein the rock sample comprises shale.

17. A system for characterizing gas adsorption of a rock sample, the system comprising:
    a gas source that pressurizes a sample chamber containing the rock sample;
    a probe that provides measurements of a nuclear magnetic resonance (NMR) response from the sample chamber as a function of pressure;
    a processor module that transforms the measurements to obtain a Langmuir pressure distribution of gas adsorption on the rock sample; and
    a user interface that displays the Langmuir pressure distribution.

18. The system of claim 17, further comprising a vacuum pump that evacuates ambient air and vapor from the sample chamber prior to pressurization.

19. The system of claim 17, wherein the gas source pressurizes the sample chamber with methane.

20. The system of claim 17, wherein the Langmuir pressure distribution is displayed as a response intensity contribution as a function of Langmuir pressure.

21. The system of claim 17, wherein the Langmuir pressure distribution is displayed as a response intensity contribution as a function of Langmuir pressure and spin-lattice relaxation time ($T_1$).

22. The system of claim 17, wherein the Langmuir pressure distribution is displayed as a response intensity contribution as a function of Langmuir pressure and spin-spin relaxation time ($T_2$).

23. The system of claim 17, wherein the Langmuir pressure distribution is displayed as a response intensity contribution as a function of Langmuir pressure and chemical shift ($\delta$).

24. The system of claim 17, wherein the Langmuir pressure distribution is displayed as a response intensity contribution as a function of Langmuir pressure and any two or more of: spin-lattice relaxation time ($T_1$), spin-spin relaxation time ($T_2$), and chemical shift ($\delta$).

25. The system of claim 17, wherein the user interface indicates a gas storage mechanism and capacity associated with each peak.

26. The system of claim 25, wherein the gas storage mechanism is indicative of a pore size or pore surface area.

27. The system of claim 25, wherein the gas storage mechanism is further indicative of adsorption energy.

* * * * *